United States Patent
Saito

(10) Patent No.: US 9,186,042 B2
(45) Date of Patent: Nov. 17, 2015

(54) ELECTRONIC ENDOSCOPE APPARATUS

(71) Applicant: OLYMPUS CORPORATION, Tokyo (JP)

(72) Inventor: Nariaki Saito, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/022,753

(22) Filed: Sep. 10, 2013

(65) Prior Publication Data

US 2014/0055587 A1  Feb. 27, 2014

Related U.S. Application Data

(63) Continuation of application No. PCT/JP2013/063805, filed on May 17, 2013.

(30) Foreign Application Priority Data

Aug. 9, 2012  (JP) .................................. 2012-177383

(51) Int. Cl.
*A61B 1/00* (2006.01)

(52) U.S. Cl.
CPC .......... *A61B 1/00105* (2013.01); *A61B 1/00114* (2013.01); *A61B 1/0011* (2013.01)

(58) Field of Classification Search
CPC ........... A61B 1/00105; A61B 1/00114; A61B 1/00117
USPC ......................................................... 348/75
See application file for complete search history.

(56) References Cited

U.S. PATENT DOCUMENTS 5,810,714 A  9/1998  Takamura et al.
5,876,326 A  3/1999  Takamura et al.
(Continued)

FOREIGN PATENT DOCUMENTS

EP  0 730 844 A1  9/1996
EP  0 739 602 A1  10/1996
(Continued)

OTHER PUBLICATIONS

Japanese Office Action dated Oct. 22, 2013 in related Japanese Patent Application No. 2013-540162.

*Primary Examiner* — William C Vaughn, Jr.
*Assistant Examiner* — Naod Belai
(74) *Attorney, Agent, or Firm* — Scully, Scott, Murphy & Presser, P.C.

(57) ABSTRACT

An electronic endoscope apparatus includes an electronic endoscope including an insertion portion, an operation portion, and a universal cord; a plurality of types of signal cables which are selectively placed between the insertion portion and a connection connector of the universal cord, have equal lengths and different diameters, and include overall shields having surface areas corresponding to the diameters; and an electromagnetic covering member which is configured to have a predetermined surface area and covers a small-diameter signal cable to form a shield reinforcing portion, the shield reinforcing portion electrically connected to the overall shield of the small-diameter signal cable causing a sum of the surface area of the shield reinforcing portion and the surface area of the overall shield of the small-diameter signal cable to be set to be equal to or larger than the surface area of the overall shield of a large-diameter signal cable.

2 Claims, 5 Drawing Sheets

(56) References Cited

U.S. PATENT DOCUMENTS

| | | | |
|---|---|---|---|
| 2006/0254801 A1* | 11/2006 | Stevens | 174/102 R |
| 2008/0051634 A1* | 2/2008 | Yamashita et al. | 600/134 |
| 2009/0292169 A1* | 11/2009 | Mitani et al. | 600/110 |

FOREIGN PATENT DOCUMENTS

| | | |
|---|---|---|
| EP | 2 123 209 A1 | 11/2009 |
| JP | 08-243077 A | 9/1996 |
| JP | 08-297250 A | 11/1996 |
| JP | 9-43520 A | 2/1997 |
| JP | 11-155809 A | 6/1999 |
| JP | 2003126029 A | 5/2003 |
| JP | 2009-279148 A | 12/2009 |
| JP | 2011-036331 A | 2/2011 |

* cited by examiner

ELECTRONIC ENDOSCOPE APPARATUS

CROSS REFERENCE TO RELATED APPLICATION

This application is a continuation application of PCT/JP2013/063805 filed on May 17, 2013 and claims benefit of Japanese Application No. 2012-177383 filed in Japan on Aug. 9, 2012, the entire contents of which are incorporated herein by this reference.

BACKGROUND OF THE INVENTION

1. Field of the Invention

The present invention relates to an electronic endoscope apparatus, an electronic endoscope of which is configured to include an image pickup apparatus at a distal end portion of an insertion portion and such that one image pickup cable selected from among a plurality of types of image pickup cables is provided inside a universal cord.

2. Description of the Related Art

Endoscopes are in widespread use in medical and industrial fields. An example of an endoscope is a so-called electronic endoscope which has, at a distal end portion of an insertion portion, a built-in image pickup apparatus for forming an endoscopic image of an inside of a patient, an inside of a structure, or the like. The electronic endoscope can perform an observation while displaying the endoscopic image on a display apparatus, such as a monitor, which is an outside apparatus.

The image pickup apparatus is connected to, for example, a video processor which is an apparatus outside the electronic endoscope through an image pickup cable. The image pickup cable is inserted through the insertion portion, an operation portion, and a universal cord in the electronic endoscope and is connected to the video processor via a connector. The universal cord is exposed to an environment which is susceptible to disturbance noise generated by a different medical instrument or the like. An overall shield which blocks noise is provided for the image pickup cable to prevent image quality degradation due to noise.

Recently, there has been a need for higher quality of an endoscopic image. Japanese Patent Application Laid-Open Publication No. 2009-279148 discloses an electronic endoscope apparatus which has achieved prevention of size increase, particularly increase in a diameter of an insertion portion, even in a case where an image pickup apparatus that can acquire a high-quality image is placed at a distal end portion of the insertion portion.

In the above-described electronic endoscope apparatus, a plurality of types of image pickup cables having equal lengths and different diameters are prepared in advance according to specifications of electronic endoscopes. Such preparation allows easy creation of a finished product suited to uses of each type of electronic endoscope and easy assembly.

SUMMARY OF THE INVENTION

An electronic endoscope apparatus according to one aspect of the present invention includes an electronic endoscope including an insertion portion, an operation portion which is provided on a proximal end side of the insertion portion, and a universal cord which extends from the operation portion so as to be connected to an external device; a plurality of types of signal cables which are selectively placed between a distal end of the insertion portion and a connection connector for the external device that is provided at the universal cord, have equal lengths and different diameters, and include overall shields having surface areas corresponding to the diameters; and an electromagnetic covering member which is configured to have a predetermined surface area and covers, as a sheath, a small-diameter signal cable having a small diameter to form a shield reinforcing portion, the shield reinforcing portion electrically connected to the overall shield of the small-diameter signal cable causing a sum of the surface area of the shield reinforcing portion and the surface area of the overall shield of the small-diameter signal cable to be set to be equal to or larger than the surface area of the overall shield of a large-diameter signal cable having a large diameter.

DETAILED DESCRIPTION OF THE PREFERRED EMBODIMENTS

Embodiments of the present invention will be described below with reference to the drawings.

Figure 1:
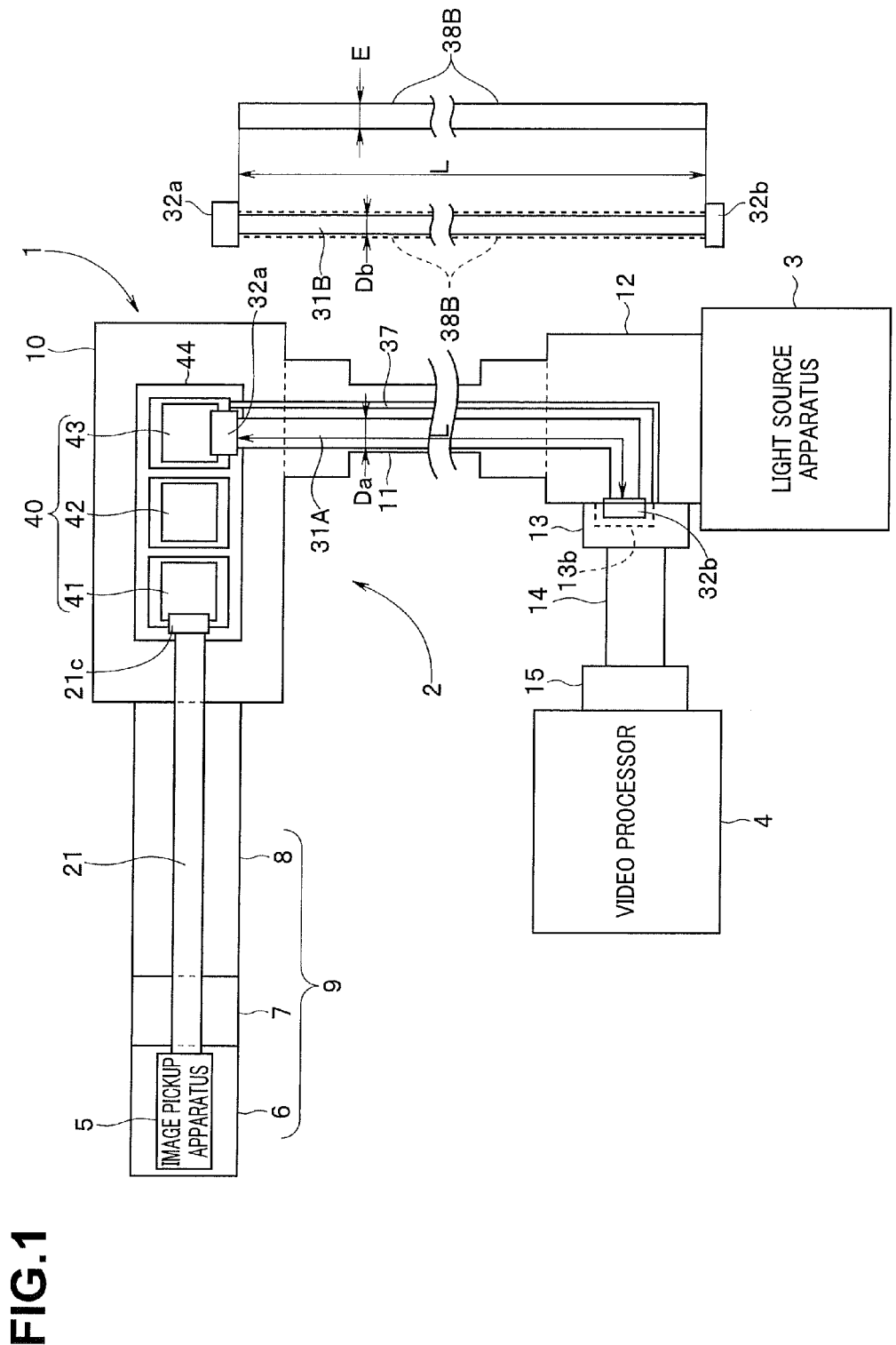
FIG. 1 is a diagram for explaining an endoscope apparatus including a large-diameter image pickup cable, a small-diameter image pickup cable, and an electromagnetic covering member.

As shown in FIG. 1, an electronic endoscope apparatus (hereinafter abbreviated as an endoscope apparatus) 1 is configured to mainly include an electronic endoscope (hereinafter referred to as an endoscope) 2, a light source apparatus 3, a video processor 4, and a display apparatus (not shown).

The endoscope 2 is configured to have an insertion portion 9, an operation portion 10, and a universal cord 11. A first universal cord-side image pickup cable (hereinafter abbreviated as a UC-side image pickup cable) 31A is inserted through the universal cord 11.

Note that a plurality of types of image pickup cables 31A and 31B corresponding to specifications of electronic endoscopes are prepared in advance for the endoscope apparatus 1 according to the present embodiment in order to ensure easy creation of a finished product suited to uses of each type of electronic endoscope and easy assembly.

That is, the second UC-side image pickup cable 31B that is shown to a right of the endoscope 2 in FIG. 1 can also be selected and be inserted through the universal cord 11, depending on specifications of an endoscope. An image pickup cable is a signal cable.

The insertion portion 9 of the endoscope 2 is configured to have a distal end portion 6, a bending portion 7, and a flexible tube portion 8 in order from a distal end. An image pickup apparatus 5 is built in the distal end portion 6.

The operation portion 10 is provided on a proximal end side of the flexible tube portion 8 constituting the insertion portion 9. A bending operation knob (not shown) for bending operation of the bending portion 7 in the insertion portion 9 is provided to be pivotable at the operation portion 10. An air/water feeding switch, a suction switch, a remote switch for, e.g., a freeze operation, a remote switch for, e.g., a release operation, and the like, all of which are not shown, are also provided at the operation portion 10. A treatment instrument insertion port (not shown) for introducing a treatment instrument into a treatment instrument channel tube is also provided at the operation portion 10.

The universal cord 11 is provided to extend from the operation portion 10 and has an endoscope connector 12 which is detachable from the light source apparatus 3 at an extending end. A cable connection portion 13 from which an electric cable 14 is detachable is provided at the endoscope connector 12. An electric connector 15 which is detachable from the video processor 4 is provided at an extending end of the electric cable 14.

The light source apparatus 3 includes, for example, a light source which supplies illuminating light to the endoscope 2. The light source is a light-emitting device, such as a lamp or an LED. In the endoscope 2 according to the present embodiment, illuminating light is transmitted by one pair of light guide bundles (denoted by reference characters 22A and 22B in, e.g., FIG. 2A (to be described later)) which are inserted through the universal cord 11, the operation portion 10, and the insertion portion 9. Distal end faces of the light guide bundles face two illuminating windows which are provided at a distal end face (not shown) of the distal end portion 6.

Note that, in a configuration in which a light-emitting device, such as an LED, is provided inside the endoscope 2, the light source apparatus 3 supplies power to the light-emitting device.

The video processor 4 converts an endoscopic image signal obtained through photoelectrical conversion by the image pickup apparatus 5 provided at the insertion portion 9 in the endoscope 2 into a predetermined video signal through signal processing and outputs the processed video signal to the display apparatus. The video processor 4 and the display apparatus are electrically connected. Video signals outputted from the video processor 4 to the display apparatus cause an observed image captured by the image pickup apparatus 5 to be displayed on a screen.

In the present embodiment, for example, three electrical circuit substrate portions 41, 42, and 43 constituting an interchange circuit 40 are provided inside the operation portion 10. The interchange circuit 40 is coated with, e.g., an electromagnetic blocking case 44 made of metal for EMC control.

Various electronic components and the like constituting, for example, a noise cancelling circuit, an amplification processing circuit which performs amplification to convert a round waveform caused by image signal degradation into a normal waveform, an A/D conversion circuit, and a D/A conversion circuit are mounted in each electrical circuit substrate portion 41, 42, or 43.

A high-speed processing circuit which processes a high-frequency endoscopic image signal is provided at the second electrical circuit substrate portion 42 located at a center in keeping with increase in the number of pixels of a picked-up image acquired by an image pickup device (not shown) of the image pickup apparatus 5.

The first electrical circuit substrate portion 41 is located on a distal end side inside the operation portion 10. An insertion portion-side image pickup cable 21 is connected to the first electrical circuit substrate portion 41 through, e.g., a connector 21c. An electric wire which supplies power to the image pickup apparatus 5 and a plurality of signal wires for delivering/receiving various signals to/from the image pickup device and transmitting the signals are inserted through the insertion portion-side image pickup cable 21.

The third electrical circuit substrate portion 43 is placed on a proximal end side inside the operation portion 10. A distal end portion of the first UC-side image pickup cable 31A is connected to the third electrical circuit substrate portion 43 through a distal end connector 32a. Note that a proximal end portion of the first UC-side image pickup cable 31A is connected to an electrical connection portion 13b inside the cable connection portion 13 through a proximal end connector 32b.

Figure 2A:
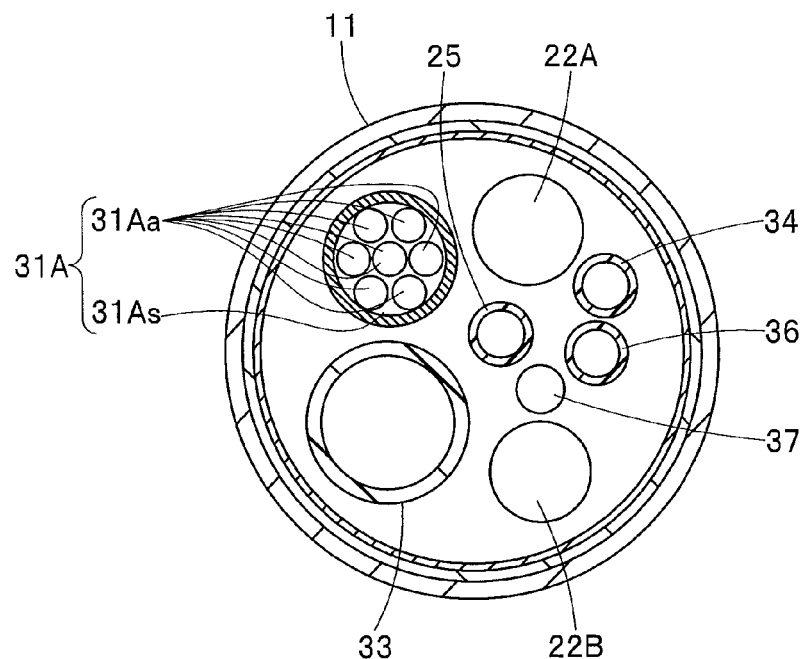
FIG. 2A is a view for explaining a universal cord through which a large-diameter image pickup cable is inserted as a cord-side built-in object.

As shown in FIGS. 1 and 2A, the first UC-side image pickup cable 31A is inserted through the universal cord 11 in the present embodiment. However, as described above, the endoscope 2 can also be configured according to endoscope specifications such that the second UC-side image pickup cable 31B is selected and is placed to be inserted through the universal cord 11, as shown in FIG. 2B.

The universal cord 11 shown in FIGS. 1 and 2A includes, as UC-side built-in objects in an inside, a suction tube 33, a cord-side water feeding tube 34, an auxiliary water feeding tube 25, a cord-side air feeding tube 36, and an electric wire 37, in addition to the first UC-side image pickup cable 31A having a length L and a diameter Da and the one pair of light guide bundles 22A and 22B.

Figure 2B:
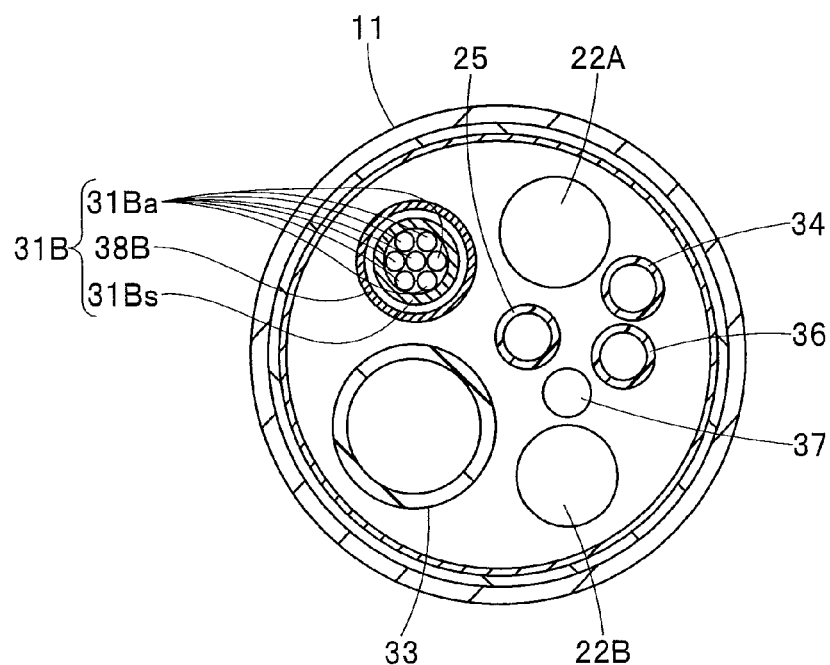
FIG. 2B is a view for explaining the universal cord through which a small-diameter image pickup cable is inserted as a cord-side built-in object.

In contrast, the universal cord 11 shown in FIG. 2B includes, in the inside, the second UC-side image pickup cable 31B covered with an electromagnetic covering member 38B for a second image pickup cable and having the length L and a diameter Db instead of the first UC-side image pickup cable 31A and includes the one pair of light guide bundles 22A and 22B, the suction tube 33, the cord-side water feeding tube 34, the auxiliary water feeding tube 25, the cord-side air feeding tube 36, and the electric wire 37 described above. The electromagnetic covering member 38B for a second image pickup cable serves as a shield reinforcing portion.

The first UC-side image pickup cable 31A and the second UC-side image pickup cable 31B that are to be inserted through the universal cord 11 have equal cable lengths and different cable diameters. More specifically, in the present embodiment, the first UC-side image pickup cable 31A is larger in diameter than the second UC-side image pickup cable 31B. In other words, the first UC-side image pickup cable 31A serves as a large-diameter image pickup cable while the second UC-side image pickup cable 31B serves as a small-diameter image pickup cable. The first UC-side image pickup cable 31A is configured to include a plurality of signal wires 31Aa and a first overall shield 31As serving as a shielding member which covers the signal wires 31Aa. The second UC-side image pickup cable 31B is configured to include a plurality of signal wires 31Ba and a second overall shield 31Bs.

Note that the first overall shield 31As is electrically connected to the connectors 32a and 32b and that the second overall shield 31Bs is electrically connected to the connectors 32a and 32b. Thus, when the distal end connector 32a of the first UC-side image pickup cable 31A is connected to the third electrical circuit substrate portion 43, and the proximal end connector 32b is connected to the electrical connection portion 13b, the first overall shield 31As is grounded via the connectors. Similarly, when the distal end connector 32a of the second UC-side image pickup cable 31B is connected to the third electrical circuit substrate portion 43, and the proximal end connector 32b is connected to the electrical connection portion 13b, the second overall shield 31Bs is grounded via the connectors.

Since the first overall shield 31As has the diameter Da and the length L, a first surface area S31As of the first overall shield 31As satisfies:

$$S31As = \pi DaL$$

In contrast, since the second overall shield 31Bs has the diameter Db and the length L, a second surface area S31Bs of the second overall shield 31Bs satisfies:

$$S3Bs = \pi DbL$$

As described above, the first UC-side image pickup cable 31A is set so as to be larger in diameter than the second UC-side image pickup cable 31B. Therefore, the first surface area S31As of the first overall shield 31As is larger than the second surface area S31Bs of the second overall shield 31Bs.

The electromagnetic covering member 38B for a second image pickup cable is provided to reinforce the second overall shield 31Bs of the second UC-side image pickup cable 31B. More specifically, the electromagnetic covering member 38B for a second image pickup cable is electrically coupled to the second overall shield 31Bs to increase the second surface area S31Bs of the second overall shield 31Bs of the second UC-side image pickup cable 31B.

Therefore, a reinforcement area S38B which is a surface area of the electromagnetic covering member 38B for a second image pickup cable is set so as to be equal to or larger than the first surface area S31As of the first overall shield 31As in a state where the electromagnetic covering member 38B for a second image pickup cable and the second overall shield 31Bs are electrically coupled.

In other words, the reinforcement area S38B of the electromagnetic covering member 38B for a second image pickup cable is set such that the expression below holds:

$$S38B + S31Bs \geq S31As$$

That is, the reinforcement area S38B of the electromagnetic covering member 38B for a second image pickup cable is an area same as or larger than a difference value between the first surface area S31As of the first overall shield 31As and the second surface area S31Bs of the second overall shield 31Bs.

Note that the electromagnetic covering member 38B for a second image pickup cable is a reticular tube which is constructed by weaving thin metallic wires having shieldability. The electromagnetic covering member 38B for a second image pickup cable is configured as an electromagnetic blocking, shield flexible tube having predetermined flexibility. The electromagnetic covering member 38B for a second image pickup cable covers the second overall shield 31Bs throughout a length, as indicated by broken lines in FIG. 1, and is electrically joined in advance to the second overall shield 31Bs.

The electromagnetic covering member 38B for a second image pickup cable has the length L and a diameter E which is larger than the diameter Db of the second UC-side image pickup cable 31B. Thus, the reinforcement area S38B satisfies:

$$S38B = \pi EL$$

According to the above-described configuration, in the electronic endoscope configured such that the first UC-side image pickup cable 31A is disposed inside the universal cord 11, external noise is blocked by the first overall shield 31As. In contrast, in the electronic endoscope configured such that the second UC-side image pickup cable 31B is disposed inside the universal cord 11, external noise is blocked by the second overall shield 31Bs and the electromagnetic covering member 38B for a second image pickup cable joined to the second overall shield 31Bs.

As described above, in the endoscope apparatus 1, where the endoscope 2 is configured such that one of the first UC-side image pickup cable 31A and the second UC-side image pickup cable 31B that are different in diameter is placed inside the universal cord 11, the second UC-side image pickup cable 31B that is a small-diameter image pickup cable is covered with the electromagnetic covering member 38B for a second image pickup cable electrically joined to the second overall shield 31Bs. The reinforcement area S38B of the electromagnetic covering member 38B for a second image pickup cable is set in advance to an area same as or larger than the difference value between the first surface area S31As of the first overall shield 31As and the second surface area S31Bs of the second overall shield 31Bs.

As a result, prevention of occurrence of a problem resulting from disturbance noise can be ensured, regardless of whether the electronic endoscope 2 is provided with the first UC-side image pickup cable 31A inside the universal cord 11 or is provided with the second UC-side image pickup cable 31B having the electromagnetic covering member 38B for a second image pickup cable electrically coupled to the second overall shield 31Bs inside the universal cord 11.

Note that there are two types of UC-side image pickup cables to be provided inside the universal cord 11 in the above-described embodiment. The number of types of UC-side image pickup cables provided inside the universal cord 11, however, is not limited to two and may be more than two.

A configuration of an endoscope apparatus 1A which includes three types of UC-side image pickup cables 31A, 31B, and 31C will be described with reference to FIGS. 3 and 4.

Figure 3:
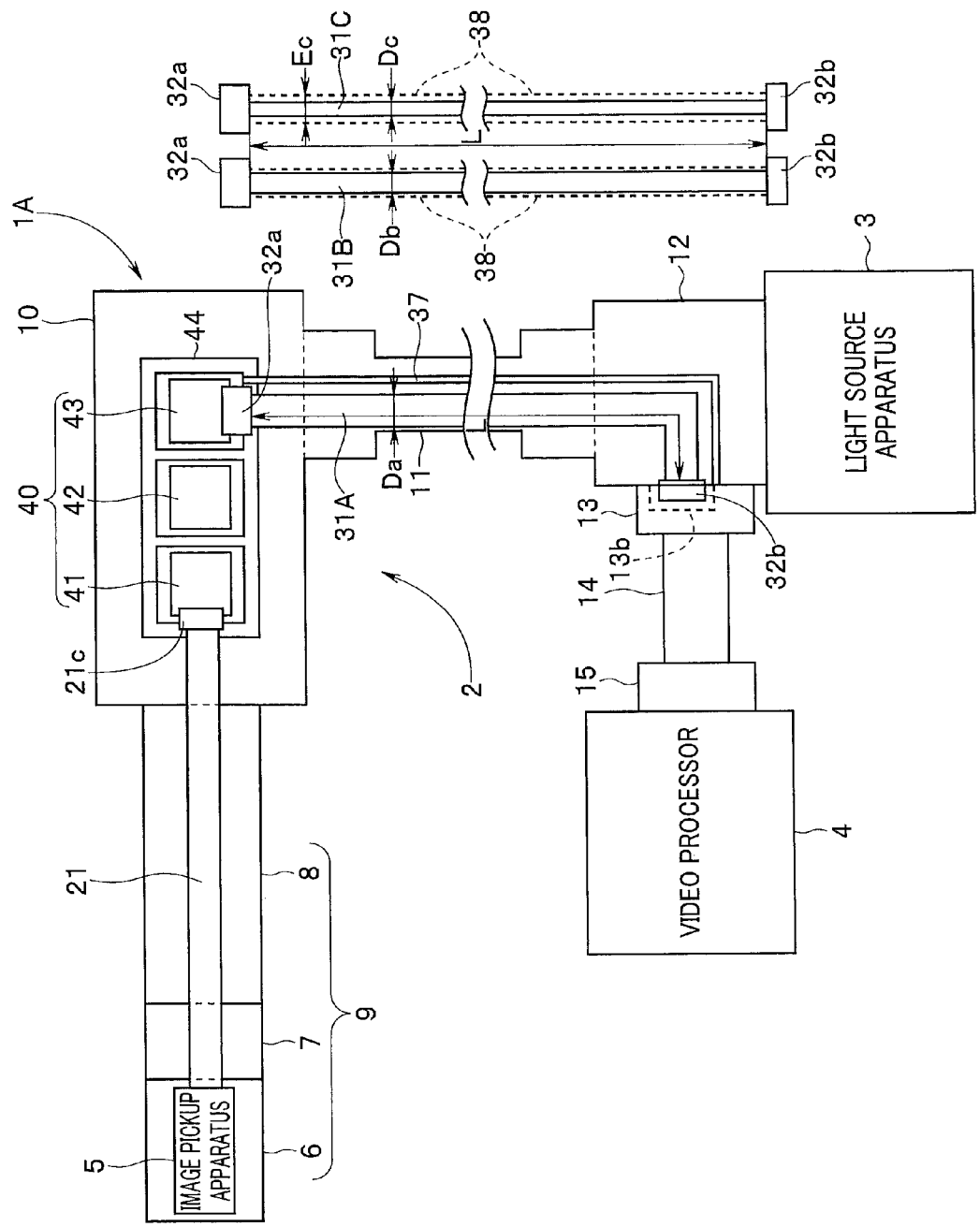
FIG. 3 is a diagram for explaining an endoscope apparatus including a large-diameter image pickup cable, a small-diameter image pickup cable, an image pickup cable intermediate in size between the large-diameter image pickup cable and the small-diameter image pickup cable, and an electromagnetic covering member.

As shown in FIG. 3, in the endoscope apparatus 1A according to the present embodiment, an endoscope 2 can be configured such that any one of the three types of UC-side image pickup cables 31A, 31B, and 31C is selected and is placed to be inserted through a universal cord 11. One electromagnetic covering member 38 which can cover the UC-side image pickup cable 31B or 31C is also provided in the present embodiment.

In the present embodiment, length of the first UC-side image pickup cable 31A, length of the second UC-side image pickup cable 31B, and length of the third UC-side image pickup cable 31C are set to an equal dimension, L. The first UC-side image pickup cable 31A has a diameter Da, the second UC-side image pickup cable 31B has a diameter Db, and the third UC-side image pickup cable 31C has a diameter Dc. The diameters Da, Db, and Dc are different from one another. More specifically, the diameters Da, Db, and Dc are set so as to become smaller in diametrical dimension in the order.

That is, the first UC-side image pickup cable 31A is a largest-outer-diameter image pickup cable. The third UC-side image pickup cable 31C is a smallest-outer-diameter image pickup cable. The second UC-side image pickup cable 31B is an intermediate-outer-diameter image pickup cable having the diameter Db intermediate between the diameter Da and the diameter Dc.

In the present embodiment, a first surface area S31As of a first overall shield 31As is πDaL, a second surface area S31Bs of a second overall shield 31Bs is πDbL, and a third surface area S31Cs of a third overall shield 31Cs is πDcL.

The first surface area S31As, the second surface area S31Bs, and the third surface area S31Cs satisfy the relationship below:

S31As>S31Bs>S31Cs

Thus, in the present embodiment, an area which is a sum of a surface area of the electromagnetic covering member 38 and the second surface area S31Bs is set to be equal to or larger than the first surface area S31As of the first overall shield 31As in a state where the electromagnetic covering member 38 is electrically coupled to the second overall shield 31Bs of the second UC-side image pickup cable 31B. Alternatively, an area which is a sum of the surface area of the electromagnetic covering member 38 and the third surface area S31Cs needs to be set to be equal to or larger than the first surface area S31As of the first overall shield 31As in a state where the electromagnetic covering member 38 is electrically coupled to the third overall shield 31Cs of the third UC-side image pickup cable 31C.

In the present embodiment, a reinforcement area S38 which is the surface area of the electromagnetic covering member 38 is set so as to be equal to or larger than the first surface area S31As of the first overall shield 31As in a state where the electromagnetic covering member 38 is electrically coupled to the third overall shield 31Cs of the third UC-side image pickup cable 31C that is a smallest-outer-diameter image pickup cable.

In other words, the reinforcement area S38 that is the surface area of the electromagnetic covering member 38 is set so as to satisfy the expression below:

S38+S31Cs≥S31As

That is, the reinforcement area S38 of the electromagnetic covering member 38 is set to an area same as or larger than a difference value between the first surface area S31As of the first overall shield 31As that is a largest-outer-diameter image pickup cable and the third surface area S31Cs of the third overall shield 31Cs. Note that the electromagnetic covering member 38 has a diameter Ec and the length L.

In the present embodiment, the electromagnetic covering members 38 are provided in advance so as to cover the second overall shield 31Bs of the second UC-side image pickup cable 31B throughout the length and to cover the third overall shield 31Cs of the third UC-side image pickup cable 31C throughout the length, as indicated by broken lines in FIG. 3.

The electromagnetic covering member 38 covering the second overall shield 31Bs is electrically joined to the second overall shield 31Bs. The electromagnetic covering member 38 covering the third overall shield 31Cs is electrically joined to the third overall shield 31Cs.

That is, in the present embodiment, the electromagnetic covering member 38 is an electromagnetic covering member common to the second UC-side image pickup cable 31B and the third UC-side image pickup cable 31C. In the present embodiment, two electromagnetic covering members 38, one for the second UC-side image pickup cable 31B and another for the third UC-side image pickup cable 31C are prepared in advance.

As a result, a shield area which is a sum of the reinforcement area S38 and the third surface area S31Cs of the third overall shield 31Cs is an area same as or larger than the first surface area S31As of the first overall shield 31As in the third UC-side image pickup cable 31C.

Since the second surface area S31Bs and the third surface area S31Cs satisfy the relationship S31Bs>S31Cs, a shield area which is a sum of the reinforcement area S38 and the second surface area S31Bs of the second overall shield 31Bs is an area larger than the first surface area S31As of the first overall shield 31As in the second UC-side image pickup cable 31B.

An inner diameter of the common electromagnetic covering member 38 is commonly set to suit an outer diameter of an intermediate-outer-diameter image pickup cable having a larger diameter so as to be attachable to a smallest-outer-diameter image pickup cable and be attachable to an intermediate-outer-diameter image pickup cable.

According to the above-described configuration, in the electronic endoscope configured such that the first UC-side image pickup cable 31A is disposed inside the universal cord 11, external noise is blocked by the first overall shield 31As. In contrast, in the electronic endoscope configured such that the second UC-side image pickup cable 31B is disposed inside the universal cord 11, external noise is blocked by the second overall shield 31Bs and the electromagnetic covering member 38 joined to the second overall shield 31Bs. In the electronic endoscope configured such that the third UC-side image pickup cable 31C is disposed inside the universal cord 11, external noise is blocked by the third overall shield 31Cs and the electromagnetic covering member 38 joined to the third overall shield 31Cs.

As described above, in the endoscope apparatus including a plurality of types of UC-side image pickup cables which are placeable inside the universal cord and have different diameters, a plurality of common electromagnetic covering members 38 are prepared. The surface area S38 of the electromagnetic covering member 38 is set to an area same as or larger than a difference value between a surface area of an overall shield of a largest-outer-diameter image pickup cable and a surface area of an overall shield of a smallest-outer-diameter image pickup cable. Additionally, an inner diameter dimension of the electromagnetic covering member 38 is made to suit an intermediate-outer-diameter image pickup cable having a largest outer diameter among a plurality of types of intermediate-outer-diameter image pickup cables, to which the electromagnetic covering members 38 are respectively attached. Each electromagnetic covering member 38 and an overall shield of each corresponding image pickup cable are electrically coupled.

As a result, if the electronic endoscope is configured such that any one of the plurality of types of UC-side image pickup cables having the different diameters is selectively provided inside the universal cord 11, prevention of occurrence of a problem resulting from disturbance noise can be ensured.

Figure 4:
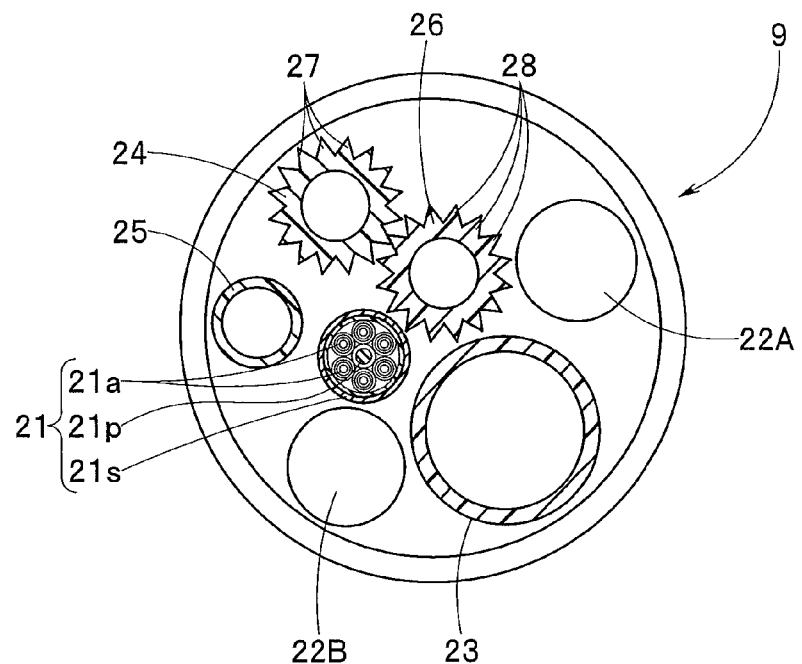
FIG. 4 is a view for explaining configurations and actions of axial protrusions which are provided on outer circumferential faces of at least two built-in objects among insertion portion-side built-in objects.

As shown in FIG. 4, for example, one pair of light guide bundles 22A and 22B, a treatment instrument channel tube 23 which doubles as a suction tube, an insertion portion water feeding tube 24, an auxiliary water feeding tube 25, an insertion portion air feeding tube 26, and the like are inserted as insertion portion built-in objects through an insertion portion 9, in addition to an insertion portion-side image pickup cable 21.

The insertion portion-side image pickup cable 21 includes a plurality of signal wires 21a and a power supply wire 21p.

The plurality of signal wires 21a and the power supply wire 21p are covered with an overall shield 21s which is a shielding member.

Figure 5:
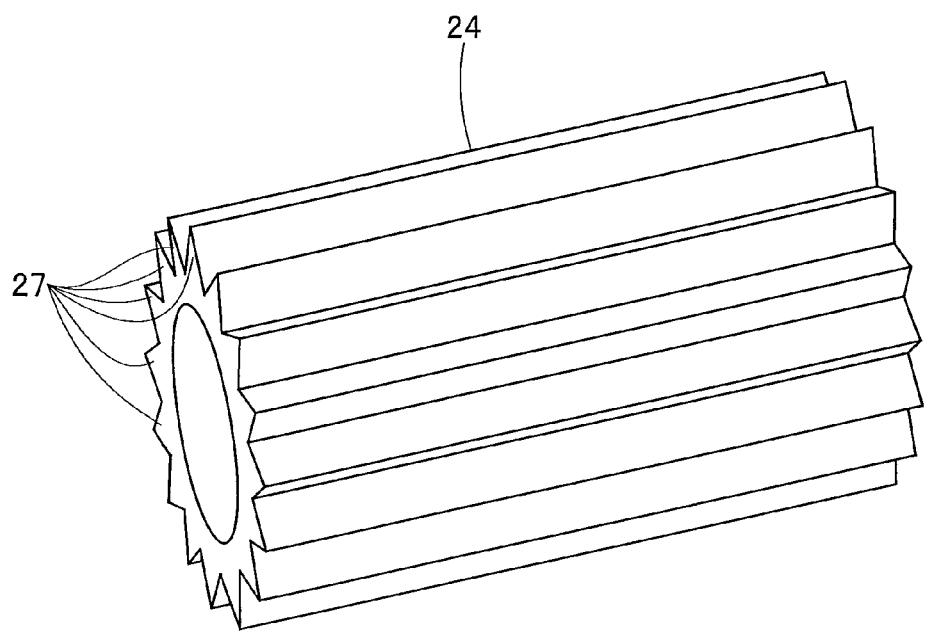
FIG. 5 is a view showing an example of a configuration of a built-in object.

As shown in FIGS. 4 and 5, for example, first axial protrusions 27 constituting a regulation portion are provided all around an outer circumferential face of the insertion portion water feeding tube 24 in the present embodiment. Second axial protrusions 28 constituting a regulation portion in a manner substantially similar to the first axial protrusions 27 are also provided all around an outer circumferential face of the insertion portion air feeding tube 26 that is provided adjacent to the insertion portion water feeding tube 24.

In the present embodiment, the first axial protrusions 27 and the second axial protrusions 28 are each in, e.g., a shape of a tooth of a gear or a triangular shape such that a plurality of first axial protrusions 27 and a plurality of second axial protrusions 28 are regularly arranged in respective circumferential directions and mesh with each other. In a state where the insertion portion water feeding tube 24 and the insertion portion air feeding tube 26 are inserted through the insertion portion 9, the first axial protrusions 27 and the second axial protrusions 28 are in a meshed condition. Ridges of the first axial protrusions 27 and ridges of the second axial protrusions 28 are placed in parallel to an insertion portion longitudinal axial direction.

According to the configuration, among the plurality of built-in objects placed inside the insertion portion 9, the first axial protrusions 27 of the insertion portion water feeding tube 24 and the second axial protrusions 28 of the insertion portion air feeding tube 26 mesh together to be integrated.

As a result, disorder in circumferential arrangement, such as interchange of circumferential positions between the insertion portion water feeding tube 24 and the insertion portion air feeding tube 26 or change in a relationship between the circumferential positions of the insertion portion water feeding tube 24 and the insertion portion air feeding tube 26, can be prevented.

As described above, disorder in circumferential arrangement of the insertion portion built-in objects inserted through the insertion portion 9 is regulated. The regulation ensures prevention of the problem of buckling of light guide bundles and various tubes or the problem of loads on image pickup cables.

Also, the placement of the ridges of the axial protrusions 27 and 28 in parallel to the insertion portion longitudinal axial direction secures axial movement of the insertion portion water feeding tube 24 and the insertion portion air feeding tube 26 meshing with each other. Additionally, inhibition of axial movement of the insertion portion water feeding tube 24 and the insertion portion air feeding tube 26 having the axial protrusions 27 and 28 and axial movement of built-in objects provided adjacent to the tubes 24 and 26 can be prevented.

As described above, provision of axial protrusions constituting a regulation portion on an outer circumferential face of an insertion portion built-in object allows elimination of disorder in arrangement of built-in objects, e.g., inside an insertion portion that is caused by conventional built-in objects having smooth outer circumferential faces.

Note that the axial protrusions 27 and 28 constituting regulation portions are provided on the outer circumferential face of the insertion portion water feeding tube 24 and the outer circumferential face of the insertion portion air feeding tube 26 in the above-described embodiment. However, axial protrusions constituting a regulation portion may be provided on an outer circumferential face of any other insertion portion built-in object or axial protrusions constituting a regulation portion may be provided on an outer circumferential face of a protective tube which protects the light guide bundle 22A or 22B. Alternatively, axial protrusions may be provided on an outer circumferential face of a universal cord built-in object.

If a circuit with low electrostatic resistance is installed on a substrate, an insulating member may be assembled to the substrate in order to protect the circuit. In the configuration, an electric insulation effect deriving from the insulating member is reliably obtained if the circuit is exposed to an environment in a dry atmosphere.

However, if the circuit is exposed to, e.g., an environment in a wet atmosphere or an environment immediately after the circuit is taken out from a wet atmosphere, a water droplet which is a conducting substance adheres to a surface or the like of the insulating member, static electricity may propagate through the adherent conducting substance and be applied to the circuit.

Figure 6:
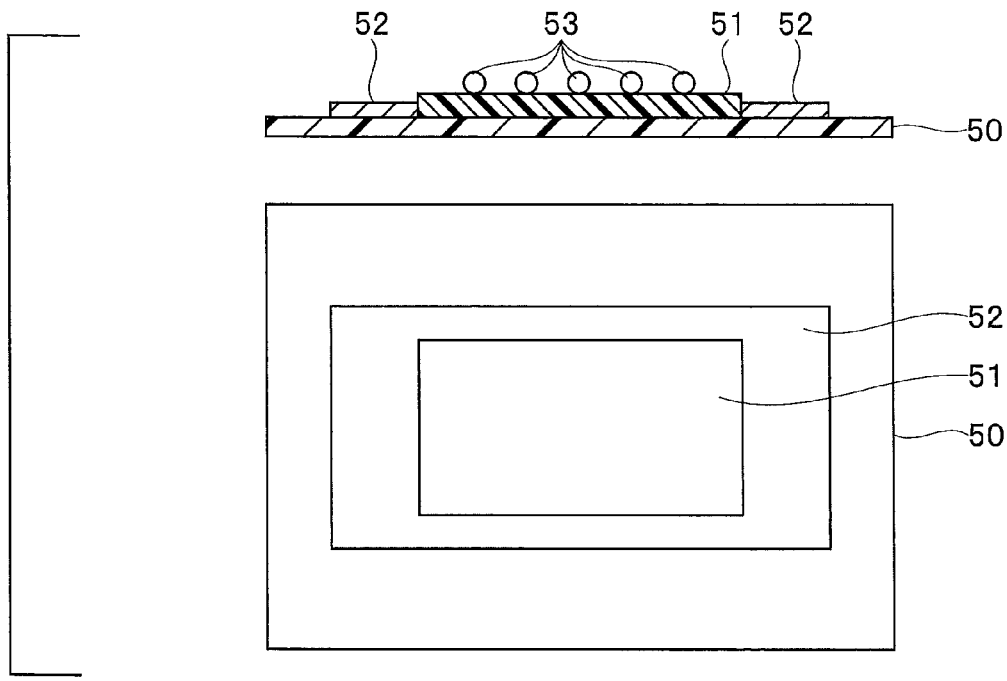
FIG. 6 are a side cross-sectional view and a top view for explaining a configuration and an action of a circuit substrate having an assembled insulating member in which a ground pattern is provided around the insulating member.

In order to eliminate the problem, a ground pattern 52 is provided around an insulating member 51 in a circuit substrate 50 shown in FIG. 6. According to the configuration, even if a conducting substance 53 adheres to a surface or the like of the insulating member 51, static electricity propagating through the adherent conducting substance 53 is dropped onto the ground pattern 52. As a result, static electricity propagating through the conducting substance 53 can be prevented from being applied to a circuit on the circuit substrate 50.

Figure 7:
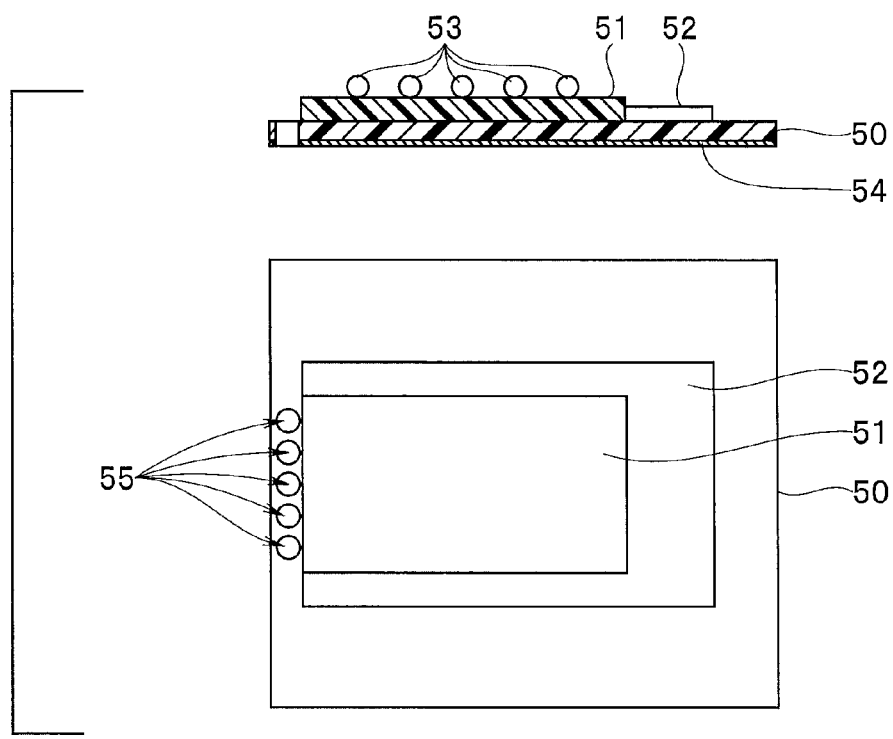
FIG. 7 are a side cross-sectional view and a top view for explaining another configuration of the circuit substrate having the assembled insulating member.

Note that if there is no space for providing the ground pattern 52 around the insulating member 51, a back face ground pattern 54 is provided all over a back face of the circuit substrate 50 provided with the insulating member 51, and a plurality of through-holes 55 are provided, as shown in FIG. 7. In the configuration, static electricity propagating through the conducting substance 53 adhering to the surface or the like of the insulating member 51 is dropped onto the ground pattern 52 or the back face ground pattern 54 through the through-holes 55. As a result, static electricity propagating through the conducting substance 53 can be prevented from being applied to the circuit on the circuit substrate 50.

Although the back face ground pattern 54 has been described as being provided all over the back face of the circuit substrate 50, the back face ground pattern 54 may be provided at a portion near the through-holes 55.

Note that the present invention is not limited to the above-described embodiments and can be modified in various manners without departing from scope of the invention.

In the above-described embodiment, an image pickup cable is divided into the insertion portion-side image pickup cable (21) and the UC-side image pickup cables (31A, 31B, and 31C) inside the operation portion (10), and the interchange circuit (40) is interposed between the insertion portion-side image pickup cable (21) and the UC-side image pickup cables (31A, 31B, and 31C). However, for example, use of the interchange circuit (40) may be ceased, and the embodiment may be configured such that a plurality of types of image pickup cables, each formed by unifying an insertion portion-side image pickup cable and a UC-side image pickup cable, are prepared and such that one of the overall shields (31As, 31Bs, and 31Cs) corresponding to the type of the relevant image pickup cable is selected and used.

What is claimed is:
1. An electronic endoscope apparatus comprising:
an electronic endoscope including an insertion portion, an operation portion which is provided on a proximal end side of the insertion portion, and a universal cord which extends from the operation portion so as to be connected to an external device;

a first image pickup cable having a predetermined length and a first diameter for connecting the operation portion and a connection connector for the external device that is provided at an end portion of the universal cord, the first image pickup cable being provided with a first overall shield having a surface area corresponding to the first diameter in order to block noise, the first image pickup cable being configured to be able to be placed in the universal cord;

a second image pickup cable having a length which is equal to the length of the first image pickup cable and a second diameter which is smaller than the first diameter for connecting the operation portion and the connection connector for the external device that is provided at the end portion of the universal cord, the second image pickup cable being provided with a second overall shield having a surface area corresponding to the second diameter in order to block noise, the second image pickup cable being configured to be able to be placed in the universal cord; and a shield reinforcing portion which covers, as a sheath, the second image pickup cable, and is electrically connected to the second overall shield provided to the second image pickup cable, the shield reinforcing portion being connected to ground, wherein a sum of the surface area of the shield reinforcing portion and the surface area of the second overall shield provided to the second image pickup cable is set to be equal to or larger than the surface area of the first overall shield provided to the first image pickup cable such that a noise blocking force of the second image pickup cable is set to be equal to or larger than a noise blocking force of the first image pickup cable.

2. The electronic endoscope apparatus according to claim 1, wherein the electromagnetic covering member is a reticular tube constituting a flexible tube which is constructed by weaving thin metallic wires having shieldability and serves as an electromagnetic blocking shield.

* * * * *